United States Patent
Pintoffl (10) Patent No.: US 10,682,118 B2
(45) Date of Patent: Jun. 16, 2020

(54) ULTRASOUND SYSTEM AND METHOD FOR ANALYZING CARDIAC PERIODICITY

(71) Applicant: General Electric Company, Schenectady, NY (US)

(72) Inventor: Klaus Pintoffl, Graz (AT)

(73) Assignee: General Electric Company, Schenectady, NY (US)

( * ) Notice: Subject to any disclaimer, the term of this patent is extended or adjusted under 35 U.S.C. 154(b) by 1183 days.

(21) Appl. No.: 14/928,133

(22) Filed: Oct. 30, 2015

(65) Prior Publication Data

US 2017/0119343 A1    May 4, 2017

(51) Int. Cl.
    *A61B 8/00*      (2006.01)
    *A61B 8/02*      (2006.01)
    *A61B 8/08*      (2006.01)

(52) U.S. Cl.
CPC .............. *A61B 8/0883* (2013.01); *A61B 8/02* (2013.01); *A61B 8/463* (2013.01); *A61B 8/486* (2013.01); *A61B 8/5207* (2013.01); *A61B 8/5223* (2013.01)

(58) Field of Classification Search
CPC ....... A61B 8/0883; A61B 8/02; A61B 8/5223; A61B 8/486; A61B 8/5207
See application file for complete search history.

(56) References Cited

U.S. PATENT DOCUMENTS

2012/0014588 A1*   1/2012   Chono ................... A61B 8/00
                                                                   382/133
2013/0150912 A1*   6/2013   Perschbacher ..... A61N 1/36585
                                                                    607/18

FOREIGN PATENT DOCUMENTS

WO     WO-2015049609 A1 *   4/2015          A61B 8/02

\* cited by examiner

*Primary Examiner* — Boniface N Nganga (57) ABSTRACT

A method and system for analyzing cardiac periodicity includes a processor, a display device, and a probe. The method and system includes acquiring ultrasound data from cardiac tissue with the probe, generating an m-mode image from the ultrasound data with the processor, displaying the m-mode image on the display device, selecting a portion of the m-mode image exhibiting periodic motion, analyzing the portion of the m-mode image with the processor to determine a cardiac periodicity, and displaying a graphical representation of the cardiac periodicity on the display device.

5 Claims, 5 Drawing Sheets

ULTRASOUND SYSTEM AND METHOD FOR ANALYZING CARDIAC PERIODICITY

FIELD OF THE INVENTION

This disclosure relates generally to an ultrasound imaging system and method for analyzing cardiac periodicity.

BACKGROUND OF THE INVENTION

Abnormal heart rhythms can be indicative of serious health problems and, as such, it is important to accurately identify them as soon as possible so that an appropriate plan of treatment or management may be implemented. It is currently difficult to accurately diagnose and quantitatively evaluate cardiac arrhythmias such as tachycardia and a "missed beat". Conventional techniques relying on ECG data are not effective for certain use cases, such as when examining a fetal heart, due to a relatively weak signal-to-noise ratio. Additionally, ECG data provides information about electrical signals traveling across the patient's heart and electrical signals are not always perfectly correlated with mechanical or hemodynamic motions of the heart. As such, it is desirable to understand the mechanical or hemodynamic motions of the patient's heart.

Ideally, the clinician would be provided with an accurate representation of a heart's mechanical or hemodynamic motions. Convention techniques relying on ultrasound data often involve a clinician viewing a cine loop based on ultrasound data and attempting to visually identify a cardiac arrhythmia. There are several problems with the conventional manual approach including high inter-operator variability, low repeatability, and an overly large dependence on the skill and experience of the operator.

For these and other reasons an improved ultrasound imaging system and method of obtaining, displaying and analyzing data regarding cardiac periodicity is desired.

BRIEF DESCRIPTION OF THE INVENTION

The above-mentioned shortcomings, disadvantages and problems are addressed herein which will be understood by reading and understanding the following specification.

In an embodiment, a method for analyzing cardiac motions with an ultrasound imaging system including a processor, a display device, and a probe includes acquiring ultrasound data from cardiac tissue with the probe. The method includes generating an m-mode image from the ultrasound data with the processor and displaying the m-mode image on the display device. The method includes selecting a portion of the m-mode image exhibiting periodic motion, automatically analyzing the portion of the m-mode image with the processor to determine a cardiac periodicity based on the periodic motion, and displaying a graphical representation of the cardiac periodicity on the display device.

In an embodiment, an ultrasound imaging system includes a probe, a display device, and a processor in electronic communication with the probe and the display device. The processor is configured to control the probe to acquire ultrasound data from cardiac tissue, generate an m-mode image from the ultrasound data, and display the m-mode image on the display device. The processor is configured to analyze a selected portion of the m-mode image exhibiting periodic motion to determine a cardiac periodicity based on the periodic motion and display a graphical representation of the cardiac periodicity on the display device.

Various other features, objects, and advantages of the invention will be made apparent to those skilled in the art from the accompanying drawings and detailed description thereof.

DETAILED DESCRIPTION OF THE INVENTION

In the following detailed description, reference is made to the accompanying drawings that form a part hereof, and in which is shown by way of illustration specific embodiments that may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken as limiting the scope of the invention.

Figure 1:
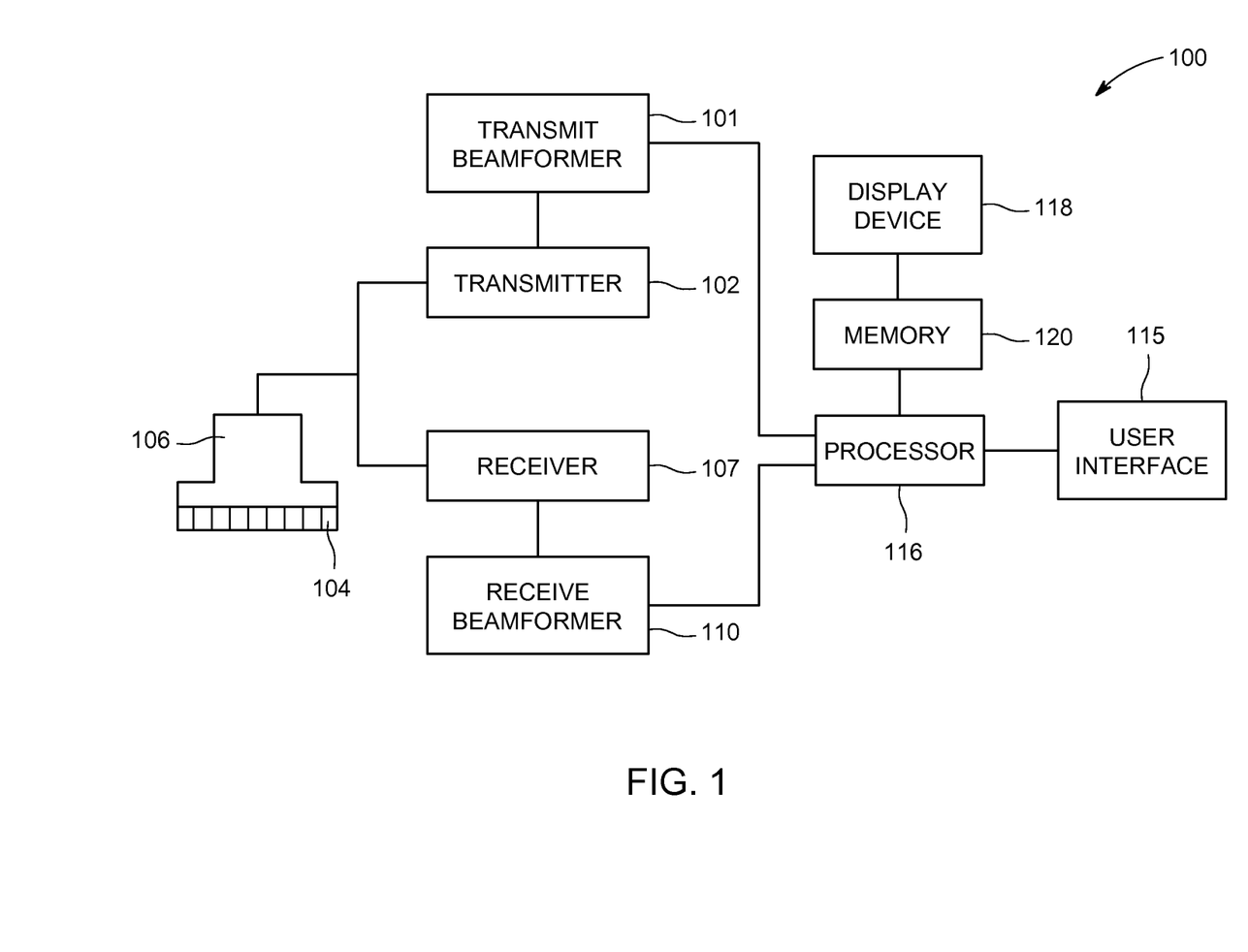
FIG. 1 is a schematic diagram of an ultrasound imaging system in accordance with an embodiment.

FIG. 1 is a schematic diagram of an ultrasound imaging system 100 in accordance with an embodiment. The ultrasound imaging system 100 includes a transmit beamformer 101 and a transmitter 102 that drive elements 104 within a probe 106 to emit pulsed ultrasonic signals. The probe 106 may be any type of probe, including a linear probe, a curved array probe, a 1.25D array probe, a 1.5D array probe, a 1.75D array probe, or 2D array probe according to various embodiments. The probe 106 may be used to acquire 2D, 3D, or 4D ultrasound data. For 3D and 4D embodiments, each acquired volume may include a plurality of 2D images or slices. Still referring to FIG. 1, the pulsed ultrasonic signals are back-scattered from structures in the body. The echoes are converted into electrical signals, or ultrasound data, by the elements 104. The ultrasound data is received by a receiver 107. The receive beamformer 110 may be a hardware component, such as an application specific integrated circuit (ASIC), a firmware component such as a field-programmable gate array (FPGA) or a software beamformer. According to some embodiments, the probe 106 may contain electronic circuitry to do all or part of the transmit beamforming and/or the receive beamforming. For example, all or part of the transmit beamformer 101, the transmitter 102, the receiver 107, and the receive beamformer 110 may be situated within the probe 106 in other embodiments. For yet another embodiment the beamforming may use phase delay or sampled delay lines for a pre-beamforming step. For embodiments where the receive beamformer 110 is a software beamformer, the receive beamformer 110 may use executable code in order to apply the appropriate delays and sum the data. The receive beamformer 110 may be a subcomponent of a processor 116 according to other embodiments. The receive beamformer 110 may be a separate module within the processor 116, or the function of the receive beamformer 110 may be performed by the processor 116. The receive beamformer 110 applies delays to the ultrasound data. The receive beamformer 110 may perform a summing operation after applying the delays to the ultrasound data. Ultrasound data may be used to refer to ultrasound data emerging from one channel (element) or a selected group of elements. The ultrasound data may include either analog or digital ultrasound data from the elements 104 or the receiver 107.

The terms "scan" or "scanning" may be used in this disclosure to refer to acquiring ultrasound data through the process of transmitting and receiving ultrasonic signals. The terms "data" and "ultrasound data" may be used in this disclosure to refer to either one or more datasets acquired with an ultrasound imaging system. A user interface 115 may be used to control operation of the ultrasound imaging system 100. The user interface 115 may be used to control the input of patient data, or to select various modes, operations, and parameters, and the like. The user interface 115 may include one or more user input devices such as a keyboard, hard keys, a touch pad, a touch screen, a track ball, rotary controls, sliders, soft keys, or any other user input devices.

The processor 116 controls the transmit beamformer 101, the transmitter 102, the receiver 107, and the receive beamformer 110. The transmit beamformer 101 may be controlled by hardware, firmware or software. The transmit beamformer 101 may also be part of the processor 116. For embodiments where the transmit beamformer 101 is a software beamformer, the transmit beamformer 101 may include one or more of the following components: a graphics processing unit (GPU), a microprocessor, a central processing unit (CPU), a digital signal processor (DSP), or any other type of processor capable of performing logical operations. And, as described above, the receive beamformer 110 may be a hardware, firmware or a software beamformer according to various embodiments. For embodiments where the receive beamformer 110 is a software beamformer, the receive beamformer 110 may include one or more of the following components: a graphics processing unit (GPU), a microprocessor, a central processing unit (CPU), a digital signal processor (DSP), or any other type of processor capable of performing logical operations controlled by a software program. The receive beamformer 110 may be configured to perform conventional beamforming techniques as well as techniques such as retrospective transmit beamforming (RTB).

The processor 116 is in electronic communication with the probe 106. The processor 116 may control the probe 106 to acquire ultrasound data. The processor 116 controls which of the elements 104 are active and the shape of a beam emitted from the probe 106. The processor 116 controls the transmit beamformer 101 and the transmitter 102 to control a focus of the transmit beams. The processor 116 controls the receiver 107, the receive beamformer 110 to perform dynamic focusing while receiving ultrasound data. The processor 116 is also in electronic communication with a display device 118, and the processor 116 may control the receive beamformer 110 to apply beamforming to the ultrasound data and perform additional processing in order to display images based on the beamformed ultrasound data on the display device 118. For purposes of this disclosure, the term "electronic communication" may include both wired and wireless connections. The processor 116 may include a central processing unit (CPU) according to an embodiment. According to other embodiments, the processor 116 may include other electronic components capable of carrying out processing functions, such as an ASIC, a digital signal processor (DSP), a field-programmable gate array (FPGA), a graphics processing unit (GPU) or any other type of processor capable of executing logical operations. According to other embodiments, the processor 116 may include multiple electronic components capable of carrying out processing functions. The processor 116 may be adapted to perform one or more processing operations on the ultrasound data according to a plurality of selectable ultrasound modalities. The ultrasound data may be processed in real-time during a scanning session as the ultrasound data is received. For the purposes of this disclosure, the term "real-time" is defined to include a procedure that is performed without any intentional delay. Real-time frame rates or volume rates may vary based on the size of the region or volume from which data is acquired and the specific parameters used during the acquisition. The data may be stored temporarily in a buffer (not shown) during a scanning session and processed in less than real-time in a live or off-line operation. Some embodiments may include multiple processors (not shown) to handle the processing tasks. Or, the processing functions attributed to the processor 116 and the receive beamformer 110 may be allocated in a different manner between any number of separate processing components, including a multi-core processor, or configurations where the processor 116 includes multiple separate processors.

According to an embodiment, the ultrasound imaging system 100 may continuously acquire ultrasound data at a frame-rate of, for example, 10 to 100 Hz. Images generated from the ultrasound data may be refreshed at a similar frame-rate. Other embodiments may acquire and display data at different rates. For example, embodiments may acquire ultrasound data at a frame rate of less than 10 Hz or greater than 100 Hz depending on the size of the volume and the intended application. A memory 120 is included for storing processed frames of acquired data. In an exemplary embodiment, the memory 120 is of sufficient capacity to store frames of ultrasound data acquired over a period of time at least several seconds in length. The frames of data are stored in a manner to facilitate retrieval thereof according to time of acquisition. The memory 120 may comprise any type of data storage medium.

Optionally, embodiments may be implemented utilizing contrast agents. Contrast imaging generates enhanced images of anatomical structures and blood flow in a body when using ultrasound contrast agents including microbubbles. After acquiring data while using a contrast agent, the image analysis includes separating harmonic and linear components, enhancing the harmonic component and generating an ultrasound image by utilizing the enhanced harmonic component. Separation of harmonic components from the received signals is performed using suitable filters. The use of contrast agents for ultrasound imaging is well-known by those skilled in the art and will therefore not be described in further detail.

In various embodiments of the present invention, data may be processed with mode-related modules by the processor 116 (e.g., B-mode, Color Doppler, M-mode, Color M-mode, spectral Doppler, Elastography, TVI, strain, strain rate, and the like) to form 2D, 3D, or 4D images or data. For example, one or more modules may generate B-mode, color Doppler, M-mode, color M-mode, spectral Doppler, Elastography, TVI, strain, strain rate and combinations thereof, and the like. The image frames are stored and timing information indicating the time of acquisition may be recorded. The modules may include, for example, a scan conversion module to perform scan conversion operations to convert the image frames from coordinates beam space to display space coordinates. A video processor module may be provided that reads the image frames from a memory and displays the image frames in real time while a procedure is being carried out on a patient. A video processor module may store the image frames in an image memory, from which the images are read and displayed.

Figure 2:
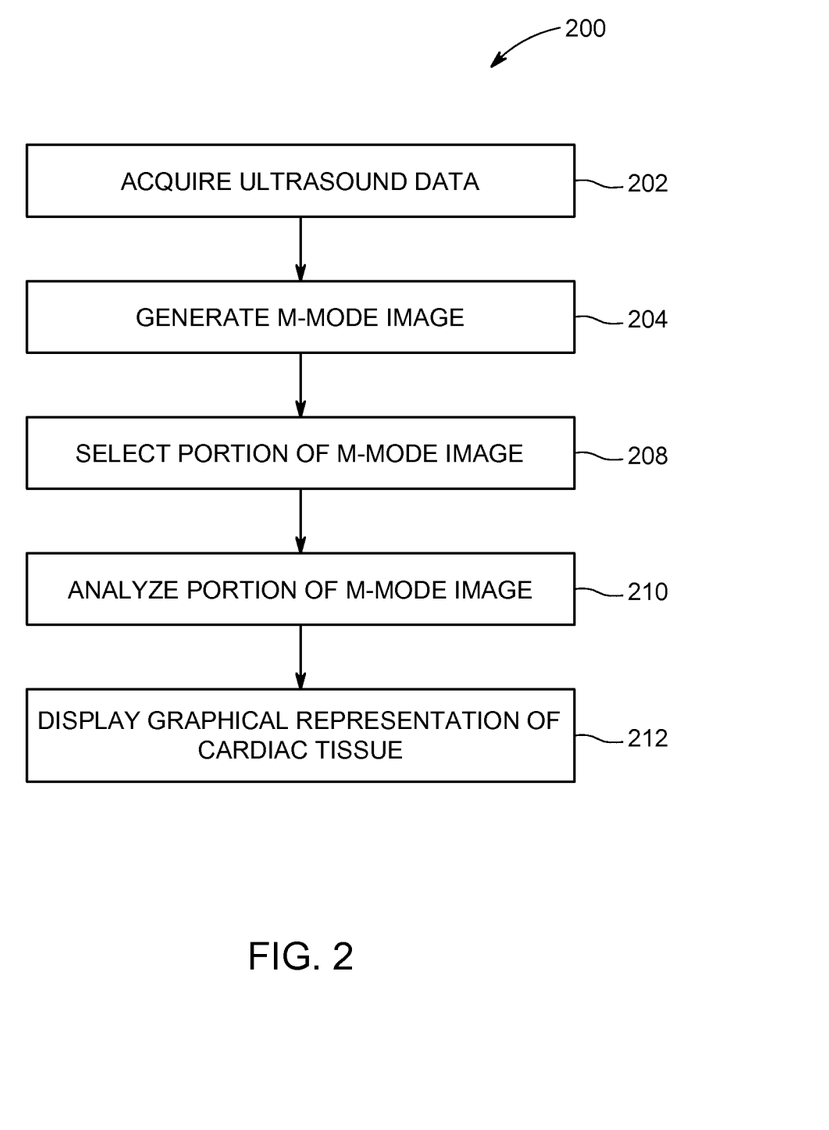
FIG. 2 is a flow chart of a method in accordance with an embodiment.

FIG. 2 is a flow chart of a method 200 in accordance with an exemplary embodiment. The individual blocks of the flow chart represent steps that may be performed in accordance with the method 200. Additional embodiments may perform the steps shown in a different sequence and/or additional embodiments may include additional steps not shown in FIG. 2. The technical effect of the method 200 is the automatic analyzing of an m-mode image and the display of a graphical representation of the cardiac periodicity.

At step 202, the processor 116 controls the transmit beamformer 101, the transmitter 102, the probe 106, the elements 104, the receiver 107, and the receive beamformer 110 to acquire ultrasound data from cardiac tissue. The ultrasound data may comprise one or more m-mode lines or the ultrasound data may comprise b-mode data. Ideally at least some of the cardiac tissue from which the ultrasound data is acquired will be experiencing periodic motion (i.e., moving in a periodic manner). According to various embodiments, the ultrasound data may include all or a portion the left ventricle, right ventricle, left atrium, right atrium, or any other portion of cardiac tissue with detectable periodic motion.

At step 204, the processor 116 generates an m-mode image from the ultrasound data acquired at step 202. If the ultrasound data is m-mode data, then processor 116 display the m-mode trace over time, such as what would be displayed in a conventional m-mode image. If the ultrasound data is b-mode data, the processor 116 may generate an image from one or more virtual m-mode traces positioned at any arbitrary angle within the b-mode image. This mode is commonly referred to as anatomic or anatomical m-mode. Those skilled in the art will appreciate that anatomic m-mode allows the user to select the position of the virtual m-mode trace in post-processing after the ultrasound data has been acquired. In contrast, the user does not have the ability to alter the position of the m-mode trace in an m-mode acquisition after the ultrasound data has been acquired. However, an m-mode image generated from m-mode data typically has a higher resolution than an anatomic m-mode image.

Figure 3:
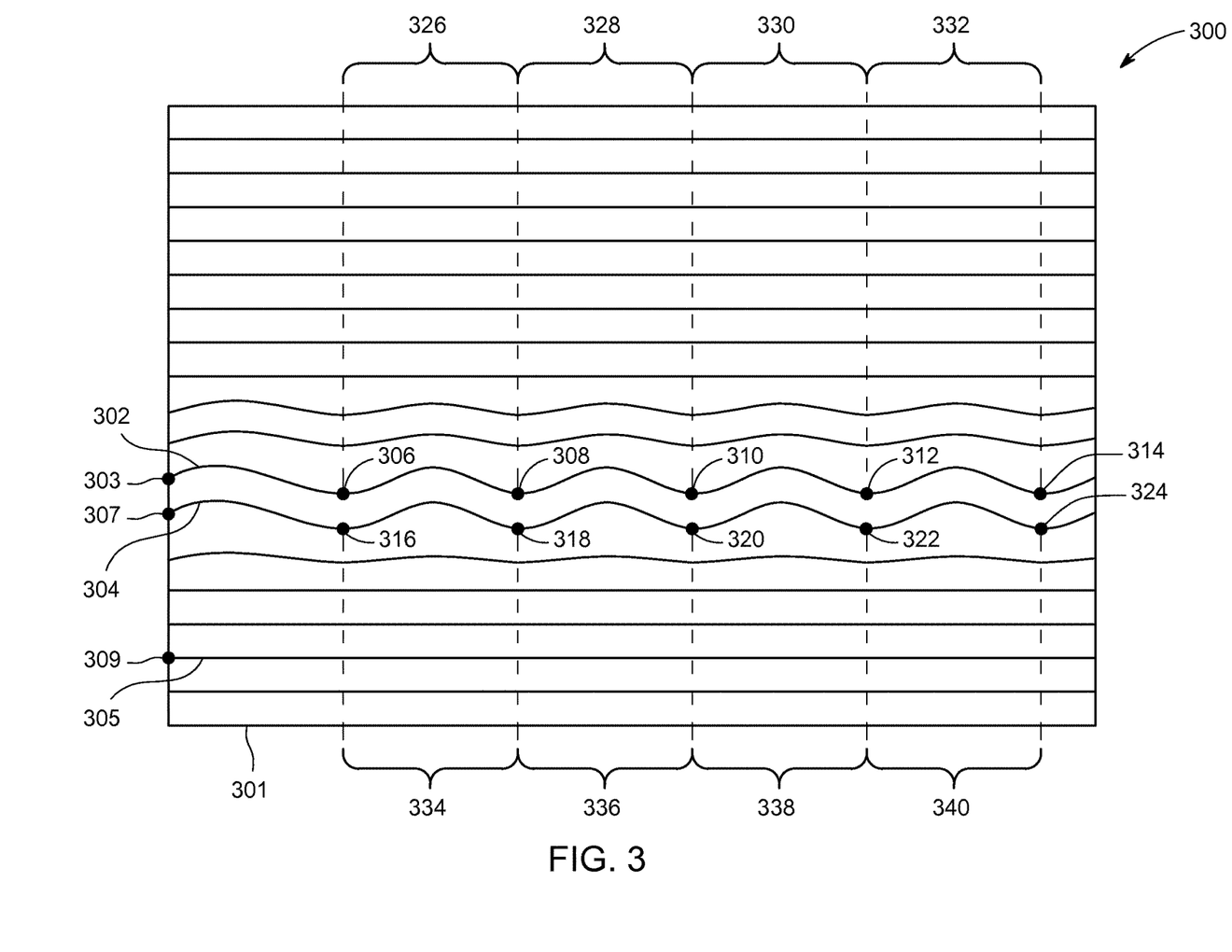
FIG. 3 is a schematic representation of a m-mode image in accordance with an embodiment.

FIG. 3 is a schematic representation of an m-mode image 300 in accordance with an embodiment. The m-mode image 300 may have been generated from either an m-mode trace or from a virtual m-mode trace generated with an anatomic m-mode. The m-mode image 300 is generated from data that includes a portion of a left ventricle, but it should be appreciated that m-mode images may include other portions of cardiac tissue according to other embodiments.

As is well-known, an m-mode image such as the m-mode image 300 illustrates how structures along the m-mode trace or anatomic m-mode trace move over time. Structures that are generally stationary are represented as a generally straight line, while structures exhibiting more motion are represented by a line that is not straight. In the m-mode image 300, time is represented along an x-axis 301. Structures exhibiting periodic motion generate a generally sinusoidal pattern in m-mode images.

At step 208, a portion of the m-mode image 300 exhibiting periodic motion is selected. The portion of the m-mode image 300 may be selected either manually or automatically. The m-mode image 300 includes a first line 302 and a second line 304. Both the first line 302 and the second line 304 exhibit periodic motion. In contrast, a third line 305 does not exhibit periodic motion. As should be appreciated with respect to FIG. 3, the term "line" as used with respect to an m-mode image does not necessarily refer to a straight line. Instead the term "line" refers to a portion of the m-mode image representing the position of a structure over the time of acquisition represented in the m-mode image.

According to an embodiment, a user may manually select the portion of the m-mode image 300 exhibiting periodic motion. For example, the user may use the user interface 115 to select either the first line 302, the second line 304, or both the first line 302 and the second line 304. According to an embodiment, the user may position a cursor or pointer on the desired line and then "click" to select the line. According to another embodiment the processor 116 may highlight the line corresponding to the position of the cursor. For example, when the cursor is positioned at point 303, the processor 116 would highlight all of line 302 in the m-mode image 300. Likewise, the processor 116 would highlight all of line 304 when the cursor is positioned at point 307, and the processor 116 would highlight all of line 305 when the cursor is positioned at point 309. Of course, points 303, 307, and 309 are just exemplary points. According to an embodiment, the processor 116 would allow the user to select the desired line by positioning the cursor anywhere on lines 302, 304, 305, or any of the other lines represented in the m-mode image 300. Additionally, the processor 116 may optionally highlight the indicated line if the cursor is positioned (hovering) over any portion of the respective line. That is, the processor 116 may highlight and/or select line 302 in response to the cursor being positioned anywhere on line 302 in the m-mode image 300.

According to another embodiment, the processor 116 may automatically select the portion of the m-mode image exhibiting periodic motion. For example, the processor 116 may implement an image processing technique on the b-mode image 300 in order to identify the portion of the b-mode image 300 exhibiting periodic motion (i.e., the line or lines of the image that are generally sinusoidal in nature). The processor 116 may use any type of image processing technique including pattern matching, deformable meshes, and/or analysis in the frequency domain, such as Fourier analysis, to identify the portion of the image exhibiting periodic motion.

At step 210, the processor 116 analyzes the portion of the m-mode image that was selected during step 208. Line 302 may represent the portion of the m-mode image 300 that was selected according to an exemplary embodiment. The processor 116 would then automatically analyze line 302. Automatically analyzing the line 302 may include automatically tracing the line 302 and identifying a plurality of corresponding points in the line. Tracing the line may involve identifying the line, such as line 302, all the way across the m-mode image 300 in a left-to-right direction. Tracing may involving showing the identified line on the m-mode image 300, or it may simply involve the step of the processor 116 identifying the entire line.

Once the processor 116 has identified the line, such as line 302, the processor 116 may identify the plurality of corresponding points such as point 306, point 308, point 310, point 312, and point 314. The processor 116 identifies the points by locating points on the line that correspond to one another. In other words, the processor 116 identifies points 306, 308, 310, 312, and 314 by identifying points along the line that are at the same relative phase when treating the line 302 like a sine wave. Points 306, 308, 310, 312, and 314 represent the local minima of line 302. It should be appreciated that the processor 116 may also identify corresponding points that are not local minima. For example, the processor 116 may identify corresponding points that are local maxima, inflection points, or any other points that may be identified as belonging to the same phase on the identified line in the m-mode image 300.

According to another embodiment, the processor 116 may identify a plurality of sets of corresponding points for each identified line. For ease of discussion, it will be assumed that the line approximates a sine curve that replicates itself every 360 degrees. The first set of corresponding points represented by points 306, 308, 310, 312, and 314 may represent a phase of 90 degrees. The second set of points, not shown, may represent 180 degrees or any phase that is different than the first set of points. Embodiments may identify any number of corresponding sets of points during step 210.

According to an embodiment, a second line such as the second line 304 may also be identified in the m-mode image 300. The second line 304 may be manually identified, automatically identified by the processor 116, or identified through a semi-automatic process. It should be appreciated that the second line 304 may be identified by any technique including those that were previously described with respect to the identification of the line 302 during step 208.

During step 210, the processor 116 may analyze the second line 304 in a manner similar to that which was described with respect to the line 302. Line 304 includes point 316, 318, 320, 322, and 324. Collectively, points 316, 318, 320, 322, and 324 define a second set of points. According to an exemplary embodiment, each point in the second set of points may be positioned at the local minima of the second line 304. However, it should be appreciated that each of the second set of points may be positioned at a different phase along the second line 304.

For embodiments where the processor 116 analyzes multiple lines during step 210, the processor 116 may average the results of the multiple lines. Depending upon the quality of the m-mode image 300, averaging the results of multiple lines and/or using multiple sets of points along each line may provide more robust data that is less sensitive to noise. For example, the processor 116 may calculate one or more time intervals between corresponding points in a first line, such as line 302, and one or more time intervals between corresponding points in a second line, such as line 304. The processor 116 may then, for example, calculate an average time interval by averaging the corresponding points for the first line 302 and the second line 304. Or according to another embodiment, the processor 116 may generate an average time interval by averaging one or more time intervals calculated between corresponding points in a first line with one or more time intervals calculated between corresponding points in a second line.

Still referring to step 210, the processor 116 may use the corresponding points (e.g., points 306, 308, 310, 312, and 314 and/or points 316, 318, 320, 322, and 324) to determine a cardiac periodicity. The term "cardiac periodicity" may be used to refer to any number of statistics describing the regularity of a patient's cardiac rhythm. As previously discussed, all the points in each set of points correspond to the same phase within the line identified in the m-mode image. Since the m-mode image 300 represents time along the x-axis 301, the processor 116 may easily determine the amount of time between each of the corresponding points based on the distance between the points in the m-mode image 300. As is well-known to those skilled in the art, the distance between adjacent points in the m-mode image 300 is directly correlated to the time between the points. For example: points 306 and 308 are separated by a distance 326; points 308 and 310 are separated by a distance 328; points 310 and 312 are separated by a distance 330; and points 312 and 314 are separated by a distance 332. Likewise, referring to the second line 304: points 316 and 318 are separated by a distance 334; points 318 and 320 are separated by a distance 336; points 320 and 322 are separated by a distance 338; and points 322 and 324 are separated by a distance 340.

The processor 116 may, for instance, use the positions of the corresponding points to determine the cardiac periodicity. A time for each of the cardiac cycles, or between adjacent cardiac cycles, may be determined from the identified corresponding points and/or based on the distances between the adjacent points, as was described previously. According to an embodiment, the processor 116 may calculate a time interval between each of the corresponding points in a line. The time interval may be, for instance, the time between adjacent corresponding points in the line. The processor 116 may determine a period of each cardiac cycle, a frequency of each cardiac cycle, or the processor 116 may determine a cardiac statistic related to the variability of the heart rhythm. For example, this may include cardiac statistics describing the how the heart rate changes over a number of cardiac cycles. An example of this may include presenting an average heart rate and then showing how the heart rate changes with respect to the average heart rate. Additionally, the processor 116 may identify cardiac cycles that are either abnormally long or abnormally short compared to the average heart rate. The processor 116 may identify a "missed beat" by identifying cardiac cycles that are too long with respect to the average heart rate. Likewise, the processor 116 may determine tachycardia, which is a heart rate that is faster than average, by examining the length of the cardiac cycles from the m-mode image 300. While the previous examples have all focused on identifying one or more cardiac cycles that are significantly different with respect to an average heart rate, it is typically undesirable to have a heart rate that is too constant. In other words, it is typically desirable to have some amount of heart rate variation in a healthy patient. The processor 116 may analyze the data regarding heart rate derived from the m-mode image and use it to determine one or more metrics regarding a patient's heart rate variability. For example, over a given time period, it is desirable to have a significant number of beats at a heart rate above the average heart rate and a significant number of beats at a heart rate below the average heart rate.

At step 212 the processor 116 displays a graphical representation of the periodicity of the cardiac tissue. The graphical representation may include a graph or a chart, such as a bar chart, a histogram, a pie-graph, a line graph, or any other type of graph or chart. According to some exemplary embodiments, the graphical representation may include one or more of cardiac beat time, beat frequency, heart rate variability, or any other variable related to cardiac periodicity. Cardiac beat time is an amount of time of each cardiac cycle or beat, beat frequency is the number of beats or cycles per unit time, such as beats per minute (BPM), heart rate variability represents the change in heart rate per unit time. Heart rate variability may be represented as a percentage change per unit time or as a change in heart rate (expressed in beats per minute, for example) per unit time.

Figure 4:
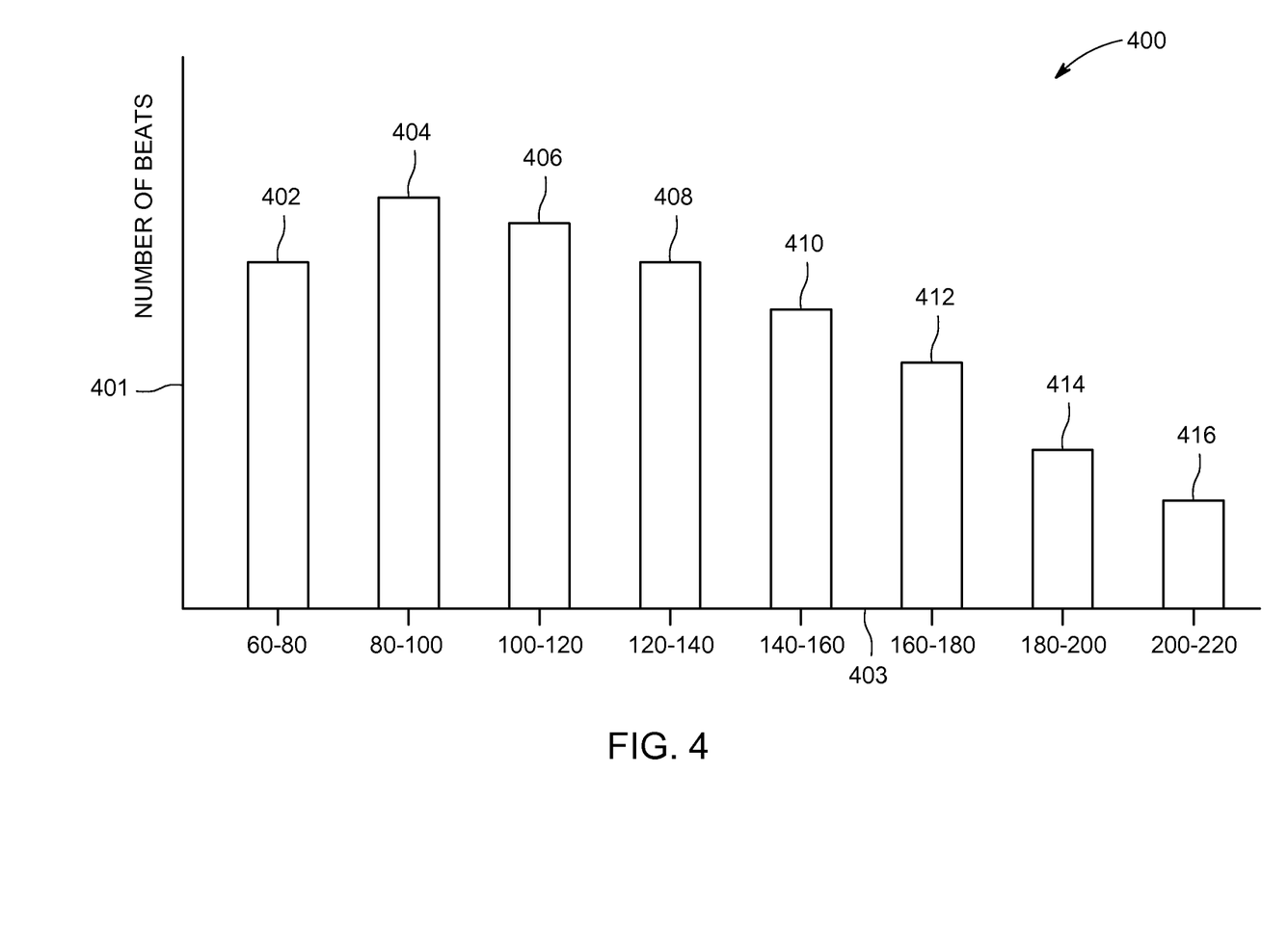
FIG. 4 is a schematic representation of a histogram in accordance with an embodiment.

FIG. 4 is a schematic representation of a histogram 400 showing the number of beats grouped by frequency. The histogram 400 is an example of a graphical representation of cardiac periodicity according to an exemplary embodiment. The histogram 400 shows the beat frequency for a specified time period. The specified time period may be user selectable or the processor 116 may use a default time period as the specified time period according to various embodiments. The number of beats is shown along a y-axis 401 and the frequency ranges for the beats is shown along an x-axis 403. A first bar 402 represent beats with frequencies from 60-80 beats per minute (bpm), a second bar 404 represents beats with frequencies from 80-100 bpm, a third bar 406 represents beats with frequencies from 100-120 bpm, a fourth bar 408 represents beats with frequencies from 120-140 bpm, a fifth bar 410 represents beats with frequencies from 140-160 bpm, a sixth bar 412 represents beats with frequencies from 160-180 bpm, a seventh bar 414 represents beats with frequencies from 180-200 bpm, and an eighth bar 416 represents beats with frequencies from 200-220 bpm.

Histogram 400 provides a quick and efficient way to convey information about the cardiac periodicity for a patient. The frequency distribution of a patient's cardiac beats is readily apparent with just a quick glance at the histogram 400. The histogram 400 allows the user to quickly assess if there are either too many or too few beats in any particular frequency range. The information in histogram 400 may help the clinician to quickly determine if the patient has experienced an arrhythmia or other undesirable cardiac event. According to other embodiments, the histogram 400 may additionally include a line or other indicator representing the average heart rate. Additionally, the histogram 400 may optionally include one or more markers indicating the expected numbers of beats for each frequency range for a "normal" patient in good health. Histogram 400 may be used for quantitatively assessing cardiac periodicity. Cardiac periodicities of different patients may be compared to one another and/or the cardiac periodicity from a first time may be compared to cardiac periodicity from a later time for a single patient. The clinician may use these markers to help make a determination if the cardiac periodicity is within an acceptable range. It should be appreciated that the histogram 400 is generated from data in a m-mode image, such as the m-mode image 300 shown in FIG. 3.

Figure 5:
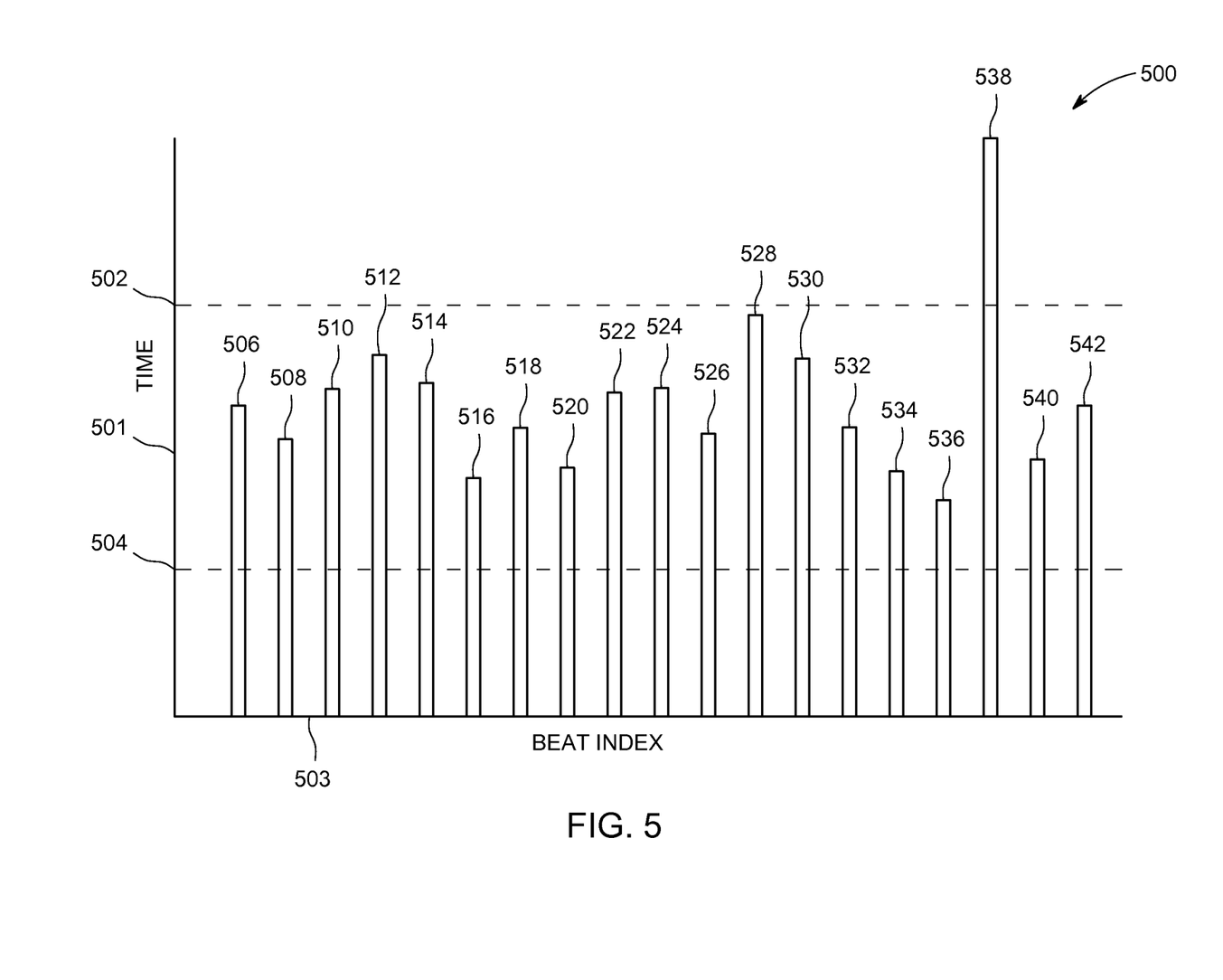
FIG. 5 is a schematic representation of a bar chart in accordance with an embodiment.

FIG. 5 is a schematic representation of a bar graph 500 in accordance with an exemplary embodiment for displaying information regarding cardiac periodicity. The bar graph 500 is an example of a graphical representation of cardiac periodicity according to an exemplary embodiment. The bar graph 500 shows cardiac beat time according to an exemplary embodiment. The bar graph 500 shows time on a y-axis 501 and a beat index on the x-axis 503. Each bar along the x-axis represents the time between corresponding portions (phases) of adjacent cardiac beats. In other words, the height of each bar represents the period for that particular cardiac beat. Data from an m-mode image, such as the m-mode image 300 shown in FIG. 3, may be used to generate the bar graph 500. The bar graph 500 includes a first bar 506, a second bar 508, a third bar 510, a fourth bar 512, a fifth bar 514, a sixth bar 516, a seventh bar 518, an eighth bar 520, a ninth bar 522, a tenth bar 524, an eleventh bar 526, a twelfth bar 528, a thirteenth bar 530, a fourteenth bar 532, a fifteenth bar 534, a sixteenth bar 536, a seventeenth bar 538, an eighteenth bar 540, and a nineteenth bar 542. The bar graph 500 also includes an upper limit 502 and a lower limit 504. The area or region between the upper limit 502 and the lower limit 504 represents a range of time for a healthy individual. If any of the bars are either above the upper limit 502 or below the lower limit 504, the clinician knows that he/she should examine those particular beats more closely for a potential arrhythmia. For example, the seventeenth bar 538 is above the upper limit 502. This may indicate a missed beat or a slowing of the patient's cardiac rhythm. All the rest of the bars fall within the acceptable range and, as such, are probably not worth further investigation by the clinician.

Each bar may represent the amount of time between corresponding points on a selected line such as the line 302 shown in FIG. 3. For example, the distance 326, between points 306 and 308 may be represented by the height of bar 506. Likewise, the distance 328, between points 308 and 310, may be represented by the height of bar 508. Nineteen different bars, each representing a different period, are represented in FIG. 5. FIG. 3 shows only 4 different time periods for line 302. The other 15 bars in bar graph 500 may represent cardiac data that is not shown in FIG. 3. For example, they may represent cardiac cycles occurring at a later time than the cardiac cycles shown in FIG. 3. The bar graph 500 may also be referred to as a beat-to-beat view since it allows for an easy comparison between adjacent beats. The bar graph 500 also provides a convenient way to quantitatively assess a patient's cardiac periodicity.

The histogram 400 shown in FIG. 4 and the bar graph 500 show in FIG. 5 are just two examples of graphical representations that may be used to represent information about cardiac periodicity for a patient. It should be appreciated that graphical representations may comprise other types of graphs or charts according to other embodiments. Additionally, various embodiments may be particularly well-suited for determining cardiac periodicity for fetal hearts, since it is known to be very difficult to collect accurate electrical data, such as an ECG, for a fetal heart.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

We claim:

1. A method for analyzing cardiac motion with an ultrasound imaging system including a processor, a display device, and a probe, the method comprising:
   acquiring ultrasound data from cardiac tissue with the probe;
   generating an m-mode image from the ultrasound data with the processor;
   displaying the m-mode image on the display device;
   selecting a portion of the m-mode image exhibiting periodic motion, wherein selecting the portion of the m-mode image exhibiting periodic motion comprises selecting a line in the m-mode image corresponding to a cardiac structure expected to exhibit periodic motion;
   automatically analyzing the portion of the m-mode image with the processor to determine a cardiac periodicity based on the periodic motion,
   wherein automatically analyzing the portion of the m-mode image comprises automatically tracing with the processor the line that was selected in the m-mode image, identifying corresponding points in the line, and calculating a time interval between each of the corresponding points in the line; and displaying a graphical representation of the cardiac periodicity on the display device.

2. A method for analyzing cardiac motion with an ultrasound imaging system including a processor, a display device, and a probe, the method comprising:
  acquiring ultrasound data from cardiac tissue with the probe;
  generating an m-mode image from the ultrasound data with the processor;
  displaying the m-mode image on the display device;
  selecting a portion of the m-mode image exhibiting periodic motion, wherein selecting the portion of the m-mode image exhibiting periodic motion comprises selecting multiple lines in the m-mode image;
  automatically analyzing the portion of the m-mode image with the processor to determine a cardiac periodicity based on the periodic motion,
  wherein automatically analyzing the portion of the m-mode image comprises tracing the multiple lines with the processor, identifying corresponding points on each of the multiple lines, calculating a time interval between the corresponding points for each of the multiple lines, and calculating an average time interval by averaging the corresponding points for the multiple lines; and
  displaying a graphical representation of the cardiac periodicity on the display device.

3. The method of claim 1, further comprising calculating a cardiac statistic based on the corresponding points and presenting the cardiac statistic on the display device.

4. The method of claim 3, wherein the cardiac statistic comprises a representation of a cardiac beat length variation, and wherein the processor is further configured display an indication of the cardiac beat length variation on the display device.

5. An ultrasound imaging system comprising:
  a probe;
  a display device; and
  a processor in electronic communication with the probe and the display device, wherein the processor is configured to:
    control the probe to acquire ultrasound data from cardiac tissue;
    generate an m-mode image from the ultrasound data;
    display the m-mode image on the display device;
    analyze a selected portion of the m-mode image exhibiting periodic motion to determine a cardiac periodicity based on the periodic motion, wherein the selected portion comprises one or more lines in the m-mode image;
  automatically trace the one or more lines in the m-mode image, identify corresponding points in the one or more lines, and calculate a time interval between the corresponding points, where the time interval represents a period of a cardiac cycle; and
  display a graphical representation of the cardiac periodicity on the display device.

* * * * *